(12) United States Patent
Putcha et al.

(10) Patent No.: US 6,716,392 B1
(45) Date of Patent: Apr. 6, 2004

(54) PRESERVATION OF LIQUID BIOLOGICAL SAMPLES

(75) Inventors: Lakshmi Putcha, Houston, TX (US); Ramalingeshwara R. Nimmagudda, Houston, TX (US)

(73) Assignee: The United States of America as represented by the United States National Aeronautics and Space Administration, Washington, DC (US)

(*) Notice: Subject to any disclaimer, the term of this patent is extended or adjusted under 35 U.S.C. 154(b) by 0 days.

(21) Appl. No.: 09/630,979

(22) Filed: Jul. 28, 2000

Related U.S. Application Data

(60) Division of application No. 09/007,239, filed on Jan. 14, 1998, now Pat. No. 6,133,036, which is a continuation-in-part of application No. 08/587,763, filed on Dec. 12, 1995, now abandoned.

(51) Int. Cl.[7] .................. G01N 1/00; G01N 31/00
(52) U.S. Cl. .................. 422/61; 422/56; 422/102; 436/8; 436/18; 436/169; 436/176; 436/177; 436/178; 435/2; 435/307.1; 252/186.25; 252/380; 252/383
(58) Field of Search .................. 436/8, 18, 165, 436/169, 176, 177, 178; 422/56–58, 61, 102, 72; 435/287.7, 287.9, 307.1, 2; 252/408.1, 186.25, 380, 383; 424/443, 452, 465, 489

(56) References Cited

U.S. PATENT DOCUMENTS

| | | | | |
|---|---|---|---|---|
| 4,636,476 A | * | 1/1987 | Brunt et al. | 436/23 |
| 4,883,679 A | * | 11/1989 | Sewón | 426/532 |
| 5,022,409 A | * | 6/1991 | Goldstein et al. | 600/573 |
| 5,103,836 A | * | 4/1992 | Goldstein et al. | 600/573 |
| 5,576,046 A | * | 11/1996 | Ellis | 426/615 |
| 5,840,356 A | * | 11/1998 | Swensen | 426/262 |

OTHER PUBLICATIONS

Stadelman et al. "Thermally Processed Hard Cooked Eggs", *Poultry Science*, vol. 61, pp. 388–391, 1982.*

Bailey et al. *Poultry Science*, vol. 66, pp. 861–865, 1987.*

* cited by examiner

Primary Examiner—Maureen M. Wallenhorst
(74) Attorney, Agent, or Firm—James M. Cate

(57) ABSTRACT

The present invention relates to the preservation of a liquid biological sample. The biological sample is exposed to a preservative containing at least about 0.15 g of sodium benzoate and at least about 0.025 g of citric acid per 100 ml of sample. The biological sample may be collected in a vessel or an absorbent mass. The biological sample may also be exposed to a substrate and/or a vehicle.

21 Claims, 2 Drawing Sheets

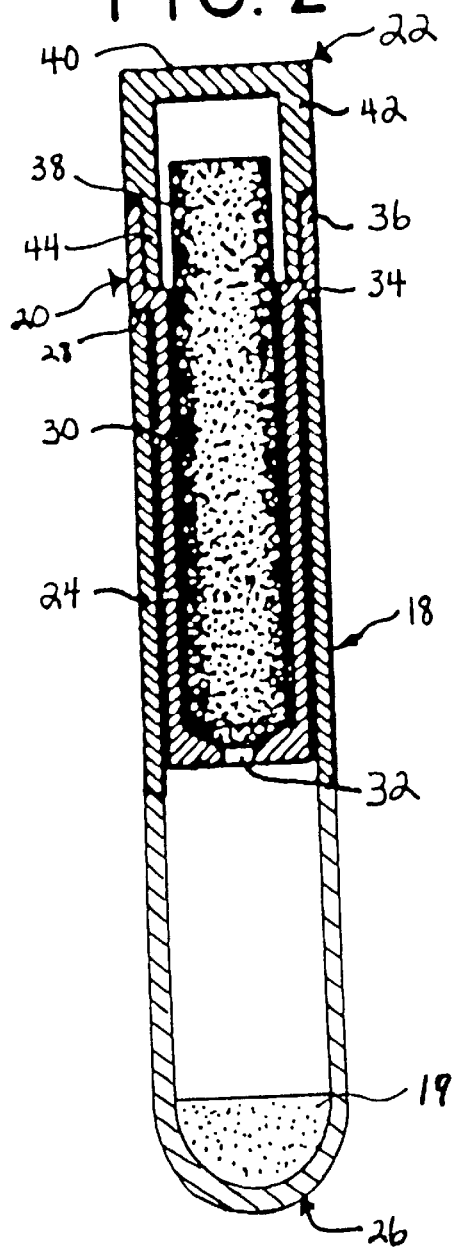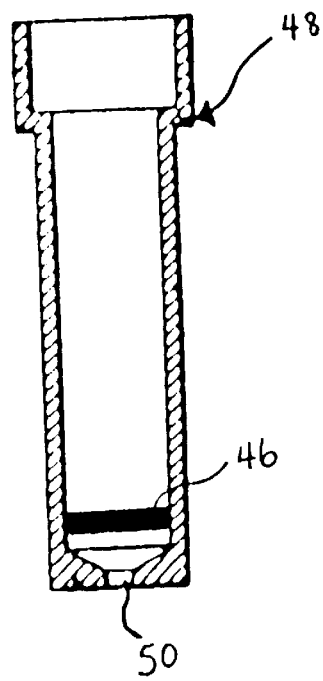

PRESERVATION OF LIQUID BIOLOGICAL SAMPLES

CROSS REFERENCE TO RELATED APPLICATIONS

This application is a divisional of application Ser. No. 09/007,239, filed on Jan. 14, 1998, now U.S. Pat. No. 6,133,036 issued on Oct. 17, 2000, which is a continuation-in-part of Ser. No. 08/587,763, filed on Dec. 12, 1995, now abandoned.

FEDERAL FUNDING LEGEND

The invention described herein was made by employees of the United States government and may be manufactured and used by or for the government of the United States of America for governmental purposes without the payment of any royalties thereon or therefore.

BACKGROUND OF THE INVENTION

1. Field of the Invention

The present invention relates generally to the fields of biochemistry and the stability and storage of biological samples. More specifically, the present invention relates to preservation of biological samples.

2. Description of the Related Art

Liquid biological samples may be utilized to test patients for a variety of medical conditions or measure in research subjects a variety of experimental variables in a non-invasive or minimally-invasive manner. Therefore, methods, apparatus and preservatives for collecting and storing liquid biological samples have widespread application in clinical and laboratory settings.

An example of a biological sampling method for saliva is disclosed in U.S. Pat. No. 4,774,962. A resilient absorbent inert body is chewed by a person and is subsequently introduced into a centrifuge tubule provided with an apertured floor. The centrifuged tubule is introduced into a centrifuge and subjected to a spinning process, whereupon the saliva is pressed out of the resilient body and passes through the floor into the lower part of the centrifuged tubule.

Another method and apparatus for collecting saliva from a test subject is disclosed in U.S. Patent No. 4,580,577. A flavored absorbent mass, such as a sponge, for mastication, is chewed by the subject charging the mass with saliva. The saliva is subsequently expressed from the mass. An apparatus for this method includes a barrel-piston arrangement in association with a specimen vial for storage until diagnostic testing.

Another sampling device disclosing a piston for compressing a porous mass containing saliva is U.S. Pat. No. 5,393,496. The sample container is inserted into the collection container and becomes fluidly coupled thereto by inserting the saliva collector into the sample container and pressing therein. This allows a sample of saliva to be collected, separated from the saliva collector and retained within the collection container for testing. The saliva collector includes a piston fitting closely within the sample container and a porous mass which may be compressed by the piston in the sample container to extract the sample of saliva for distribution to the collection container. A buffering solution may be retained within the sample container for mixing with the sample of saliva.

U.S. Pat. No. 5,376,337 discloses a saliva testing device including a sample container opened at one end, a tube, a piston, a holding reservoir and a filter. The piston is fixed to a first end of the tube on a first side of the piston and has a hole in fluid communication with the tube. The piston fits closely and slidably within the sample container. An absorbent pad is affixed to the piston on a second side thereof in fluid communication with the hole in the piston. The holding reservoir is in fluid communication with a second end of the tube. The filter is in fluid communication with a second end of the tube. The absorbent pad receives a sample of fluid to be tested. When the piston is slidably inserted into the sample container, a pressure is generated forcing the saliva of fluid into the holding reservoir through the tube.

U.S. Pat. No. 5,380,492 discloses a saliva sampling device including a sample container, a cap, a sample collector and a sample adequacy system. The sample container has an inner wall surface and a retaining ridge which is disposed on the inner wall surface. The sample collector includes a piece of filter paper and a holder which has a tube and a paddle coupled to the piece of filter paper. The paddle has a peripheral edge for engaging the retaining ridge of the sample container. The cap has an outer wall surface and an inner wall surface. The outer surface snugly engages the inner wall surface of the sample container. The inner wall surface has a truncated conical portion having a top and a cylindrical portion which is coupled to the truncated conical portion adjacent to the top thereof. The truncated conical portion thereof slidably engages the tube in order to guide the tube so that the cylindrical portion thereof snugly engages the tube.

U.S. Pat. No. 4,938,963 to Parnell teaches the use of citric acid and sodium benzoate to stimulate saliva production and to facilitate the use of the Yerba Santa fluid extract of the lozenge, respectively. U.S. Pat. No. 5,022,409 to Goldstein teaches an oral rinse for the collection of immunoglobulins and other substances from saliva and U.S. Pat. No. 5,103,836 to Goldstein teaches a kit and apparatus for the collection of saliva samples. However, in both of these patents of Goldstein, citric acid is used exclusively as a saliva production stimulator. Furthermore, the presence of sodium benzoate is meaningless because each device is adjusted to a final pH of 6.5 and as is well known in this art, sodium benzoate is not effective as a preservative at pH values above 4.0.

The prior art is deficient in the lack of effective means of preserving a biological sample containing analytes, e.g., proteins, lipids and carbohydrates. The present invention fulfills this longstanding need and desire in the art.

SUMMARY OF THE INVENTION

Generally, the invention features a preservative for liquid biological samples including sodium benzoate in an amount of at least about 0.15% of the sample (weight/volume) and citric acid in an amount of at least about 0.025% of the sample (weight/volume). Embodiments of this aspect of the invention may include one or more of the following features. The amount of sodium benzoate and citric acid may range between about 0.15% to about 1.00% and about 0.025% to about 0.200% of the sample (weight/volume), respectively. The preservative may be a solid. The preservative may be disposed within a vessel for storing the sample. The preservative may be coupled operatively to an absorbent mass for collecting the sample. The preservative may be coupled operatively to a substrate which may be combined with a sample after collection. The preservative may be coupled operatively to a vehicle prior to sample collection. The liquid biological sample may be saliva, tears, urine, blood, serum, plasma, sweat, vaginal fluids, semen, feces, mucous, breast milk, ascites, lymph, pleural effusion, synovial fluid, bone narrow, spino-cerebral fluid, and washings from bodily cavities (e.g., lung washings).

In general, in another aspect, the invention features a kit for preserving a liquid biological sample including a sample collecting device and a preservative coupled operatively to the device, the preservative including sodium benzoate and citric acid in an amount of about 0.15% to about 1.00% and about 0.025% to about 0.200% of the sample (weight/volume), respectively. Embodiments of the aspect of the invention featuring a kit combining a sample collecting device and a preservative coupled operatively thereto may include one or more of the following features. The sample collecting device may be a vessel. The sample collecting device may be an absorbent mass.

In general, in another aspect, the invention features a kit for preserving a liquid biological sample including a preservative carrier and a preservative coupled operatively to the carrier, the preservative including sodium benzoate and citric acid in an amount of about 0.15% to about 1.00% and about 0.025% to about 0.200% of the sample (weight/volume), respectively. Embodiments of the aspect of the invention featuring a kit combining a preservative carrier and a preservative coupled operatively thereto may include one or more of the following features. The carrier may be a substrate. The carrier may be a vehicle.

In another aspect, the invention features the combination of a vessel and a preservative disposed within the vessel, the preservative including sodium benzoate and citric acid in an amount of about 0.15% to about 1.00% and about 0.025% to about 0.200% of the sample (weight/volume), respectively. Embodiments of the aspect of the invention featuring the combination of a vessel and a preservative disposed therein may include one or more of the following features. The preservative may be a solid. The preservative may be deposited on an interior surface of the vessel. The preservative may be deposited by vacuum drying a solution including sodium benzoate and citric acid. The vessel may include an upper chamber separated by a liquid permeable partition from a lower chamber in which the preservative is disposed and further include an absorbent mass for collecting the sample, the mass being insertable into the upper chamber such that the sample may be separated into the lower chamber and mixed with the preservative. The sample may be separated by centrifugation.

In general, in another aspect, the invention features the combination of an absorbent mass for collecting the sample and a preservative coupled operatively to the mass, the preservative including sodium benzoate and citric acid in an amount of about 0.15% to about 1.00% and about 0.025% to about 0.200% of the sample (weight/volume), respectively. Embodiments of the aspect of the invention featuring the combination of an absorbent mass and a preservative coupled operatively thereto may include one or more of the following features. The mass may be impregnated with the preservative. The combination may include a vessel having an upper chamber separated by a liquid permeable partition from a lower chamber, the mass being insertable into the upper chamber such that following collection the sample may be separated into the lower chamber. The sample may be separated by centrifugation.

In general, in another aspect, the invention features the combination of a substrate and a preservative coupled operatively to the substrate, the preservative including sodium benzoate and citric acid in an amount of about 0.15% to about 1.00% and about 0.025% to about 0.200% of the sample (weight/volume), respectively. Embodiments of the aspect of the invention featuring the combination of a substrate and a preservative coupled operatively thereto may include one or more of the following features. The combination may include a vessel within which the substrate is disposed. The vessel may include an upper chamber separated by a liquid permeable partition from a lower chamber. The substrate may be disposed within the upper chamber.

In another aspect of the invention there is provided a method of preserving a liquid biological sample, in which a liquid biological sample is provided and the sample is combined with a preservative including sodium benzoate and citric acid in an amount of about 0.15% to about 1.00% and about 0.025% to about 0.200% of the sample (weight/volume), respectively. Embodiments of the aspect of the invention featuring a method of preserving a liquid biological sample may include, after the sample is provided, one or more of the following features. The method may include introducing the sample into a vessel. The preservative may be disposed within the vessel prior to introducing the sample. The preservative may be a solid. The preservative may be deposited on an interior surface of the vessel. The preservative may be deposited by vacuum drying a solution including sodium benzoate and citric acid onto the interior surface.

The method may also include, after providing the sample, collecting the sample with an absorbent mass. The preservative may be coupled operatively to the mass. The method may include, after combining the sample with the preservative, separating the sample from the mass. Separating may be accomplished by inserting the mass into a vessel including an upper chamber separated by a liquid permeable partition from a lower chamber and centrifuging the vessel so that the sample passes through the partition into the lower chamber and the mass is retained in the upper chamber. The method may include, after collecting the sample, separating the sample from the mass. Separating may be accomplished by inserting the mass into a vessel including an upper chamber separated by a liquid permeable partition from a lower chamber into which the preservative is disposed and centrifuging the vessel so that the sample passes through the partition into the lower chamber and the mass is retained in the upper chamber.

The method may also include combining the sample with a preservative which is coupled operatively to a substrate. The substrate may be disposed within a vessel. The vessel may include an upper chamber separated by a liquid permeable partition from a lower chamber. The substrate may be disposed within the upper chamber. Combining may be accomplished by introducing the sample into the upper chamber and centrifuging the vessel so that the sample passes through the substrate into the lower chamber. The method may include, after providing the sample, collecting the sample in an absorbent mass.

In another aspect, the invention features a method of preserving a saliva sample in which a preservative is introduced into the oral cavity of a mammal and a saliva sample is collected from the mammal. Embodiments of the aspect of the invention featuring a method of preserving a saliva or plasma sample may include one or more of the following features. The preservative may include sodium benzoate and citric acid in an amount of about 0.15% to about 1.00% and about 0.025% to about 0.200% of the sample (weight/volume), respectively. The preservative may be coupled operatively to a vehicle. The vehicle may be a paste, a powder, a liquid, a gel, a tablet or a capsule.

Among the following advantages of the invention may be one or more of the following. Liquid biological samples preserved according to the present invention may be stored for extended periods without refrigeration or freezing. Therefore, samples may be easily obtained and preserved for analysis in a variety of remote locations (e.g., during space travel, field research and non-clinical health care settings).

In addition, vacuum drying increases significantly the shelf life of the preservative and facilitates easy storage and transportation of vessels, substrates, absorbent masses or other materials to which the preservative is coupled (e.g., by eliminating spillage problems). Moreover, because the preservative is edible it may be applied directly to an absorbent mass or introduced directly into the oral cavity of a subject from which a saliva sample is desired.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 is a sectional view of an apparatus for preserving liquid biological samples.

FIG. 3 is a sectional view of a collection device.

DETAILED DESCRIPTION OF THE INVENTION

Figure 1:
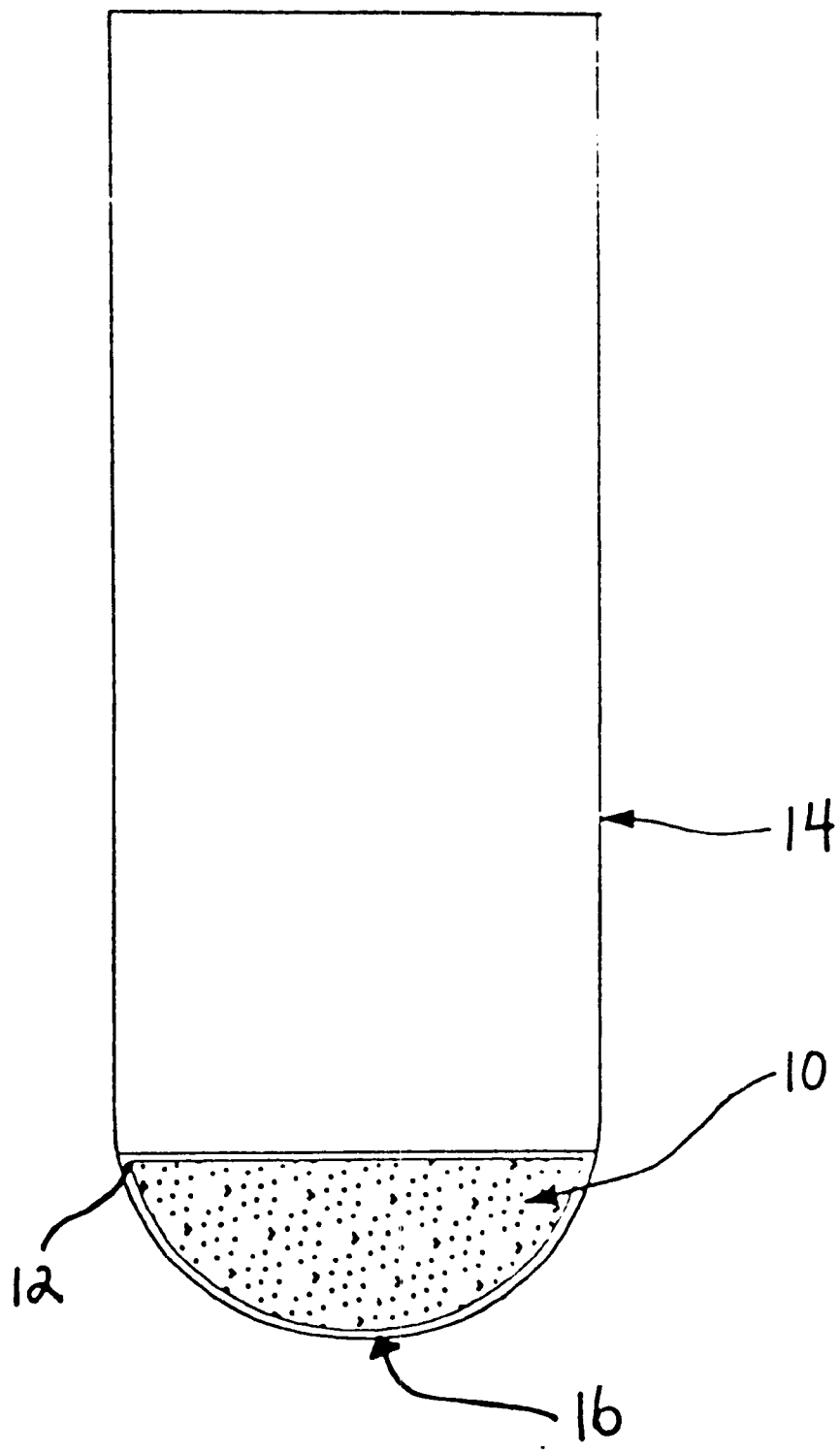
FIG. 1 is a side view of a storage vessel.

One aspect of the invention is a preservative for liquid biological samples containing at least about 0.15% sodium benzoate (weight/volume of sample) and at least about 0.025% citric acid (weight/volume of sample). A range of about 0.15% to about 1.00% sodium benzoate (weight/volume of sample) and about 0.025% to about 0.200% citric acid (weight/volume of sample) is preferred. Concentrations expressed as a percent solution reflect the number of grams of solute (e.g., sodium benzoate or citric acid) in 100 milliliters of solvent (e.g., liquid biological samples). For example, 0.15% sodium benzoate (weight/volume of sample)=0.15 grams of sodium benzoate in 100 milliliters of saliva.

The preservative is effective for preserving saliva, plasma and a variety of liquid biological samples including, but not limited to, tears, urine, blood, serum, sweat, vaginal fluids, semen, feces, mucous, lymph, breast milk, ascites, pleural effusion, synovial fluid, bone marrow, spino-cerebral fluid, and washings from bodily cavities (e.g., lung washings). The preservative is preferably supplied as a dry solid, but may be supplied in a variety of forms (e.g., paste, liquid, gel, capsule or tablet) which are compatible with the liquid biological sample to be preserved and the methods or apparatus used for preserving the sample (see detailed descriptions below). The dry solid preservative is preferably disposed within a vessel for collecting and/or storing the sample. For example, amounts of dry solid sodium benzoate and citric acid appropriate to achieve the desired concentration range in a given volume of sample may be weighed on an analytical balance.

Alternatively, a solution containing sodium benzoate and citric acid may be aliquoted into a vessel and dried so as to deposit the preservative on an interior surface of the vessel. The volume aliquoted will depend upon the concentration of the solution, the desired final concentration of preservative and the volume of the sample. Alternatively, the preservative may be coupled to an absorbent mass for collecting and/or storing the sample. It may also be coupled to a substrate (e.g., a filter, a membrane, or other material to which the preservative may be releasably bound) to be combined with the sample. Preferred substrates include ten millimeter diameter disks of Whatman No. 1 filter paper or polyethylene terethalate. The preservative also may be incorporated within a vehicle (e.g., a paste, powder, liquid, gel, tablet or capsule) which may be combined with the sample either prior to or after collection. Because the preservative is edible, it may be applied directly to an absorbent mass for collecting the sample or introduced directly into the oral cavity of a subject from which a saliva sample is desired.

The following examples are given for the purpose of illustrating various embodiments of the invention and are not meant to limit the present invention in any fashion.

EXAMPLE 1

A Preservative for Saliva Samples

Non-invasive estimates of physiological and pharmacokinetic alterations may be obtained by measuring the concentrations of certain compounds and their metabolites in liquid biological samples (e.g., saliva). For example, gastrointestinal activity and the absorption, bioavailability and elimination of acetaininophen ("APAP") may be assessed by measuring APAP concentrations in liquid biological samples following oral administration of APAP. In addition, hepatic metabolism may be measured indirectly from the clearance of orally administered antipyrine ("AP") from liquid biological samples. The accuracy of such non-invasive estimates depends, in part, upon the stability of the reference compound or metabolite in the liquid biological sample. Therefore, the effectiveness of a particular preservative may be evaluated by determining the degradation time course for a known quantity of a specific reference compound.

The effectiveness of the preservative of the present invention was evaluated by measuring the stability of APAP and AP in saliva samples stored at $-20°$ C. as compared to saliva samples stored at room temperature and containing sodium benzoate and citric acid in an amount of 0.25% and 0.05% of the sample (weight/volume), respectively ("P1"). Saliva samples were collected from forty subjects, pooled, aliquoted and spiked with APAP (5 or 25 $\mu$g/ml) or AP (5 or 50 $\mu$g/ml). Duplicate samples were analyzed by high performance liquid chromatography on days 1, 14, 28, 60, 120, 180, 240 and 360 (see Tables 1–4 below). APAP and AP concentrations were comparable in saliva samples stored for at least 360 days at $-20°$ C. and at room temperature in the presence of P1.

TABLE 1

Saliva Stability Of 5 $\mu$G/ml Antipyrine (AP) Under Varied Preservation Conditions

| Time | AP-P1* [RT] | No Preservative [$-20°$ C.] |
|---|---|---|
| Day 01 | 6.28 ± 0.65 | 6.05 ± 0.49 |
| Day 14 | 5.04 ± 0.08 | 5.37 ± 0.06 |
| Day 28 | 5.51 ± 0.05 | 5.68 ± 0.13 |
| Day 60 | 6.00 ± 0.15 | 5.13 ± 0.04 |
| Day 120 | 5.06 ± 0.78 | 5.79 ± 0.86 |
| Day 180 | 4.71 ± 0.31 | 5.09 ± 0.00 |
| Day 240 | 3.92 ± 0.19 | 5.18 ± 0.25 |
| Day 360 | 4.67 ± 0.54 | 5.33 ± 0.01 |

*P1 is a mixture of Sodium Benzoate (0.25%) + Citric acid (0.05%); and RT is room temperature.

TABLE 2

Saliva Stability Of 50 μg/ml Antipyrine (AP) Under Varied Preservation Conditions

| Time | AP-P1* [RT] | No Preservative [−20° C.] |
| --- | --- | --- |
| Day 01 | 52.07 ± 8.4 | 46.15 ± 2.6 |
| Day 14 | 53.95 ± 1.17 | 48.67 ± 0.05 |
| Day 28 | 52.31 ± 0.75 | 49.44 ± 0.06 |
| Day 60 | 51.20 ± 1.56 | 47.98 ± 0.05 |
| Day 120 | 45.16 ± 0.47 | 48.80 ± 0.84 |
| Day 180 | 48.34 ± 1.83 | 47.02 ± 1.17 |
| Day 240 | 43.62 ± 0.52 | 45.34 ± 0.14 |
| Day 360 | 49.29 ± 0.13 | 48.12 ± 2.67 |

*P1 is a mixture of Sodium Benzoate (0.25%) + Citric acid (0.05%); and RT is room temperature.

TABLE 3

Saliva Stability Of 5 μg/ml Acetaminophen (APAP) Under Varied Preservation Conditions

| Time | APAP-P1* [RT] | No Preservative [−20° C.] |
| --- | --- | --- |
| Day 01 | 5.49 ± 0.09 | 5.83 ± 0.08 |
| Day 14 | 5.38 ± 0.14 | 6.59 ± 0.61 |
| Day 28 | 4.83 ± 1.79 | 5.81 ± 0.08 |
| Day 60 | 6.89 ± 0.94 | 5.82 ± 0.20 |
| Day 120 | 5.40 ± 0.20 | 5.54 ± 0.33 |
| Day 180 | 4.37 ± 0.08 | 3.77 ± 0.03 |
| Day 240 | 4.29 ± 0.25 | 4.17 ± 0.16 |
| Day 360 | 5.31 ± 0.43 | 5.14 ± 0.09 |

*P1 is a mixture of Sodium Benzoate (0.25%) + Citric acid (0.05%); and RT is room temperature.

TABLE 4

Saliva Stability Of 25 μg/ml Acetaminophen (APAP) Under Varied Preservation Conditions

| Time | APAP-P1* [RT] | No Preservative [−20° C.] |
| --- | --- | --- |
| Day 01 | 24.94 ± 0.56 | 24.88 ± 0.22 |
| Day 14 | 24.63 ± 0.12 | 25.60 ± 0.41 |
| Day 28 | 27.3 ± 1.54 | 25.25 ± 0.48 |
| Day 60 | 29.88 ± 3.58 | 25.02 ± 0.4 |
| Day 120 | 24.20 ± 0.47 | 25.45 ± 0.49 |
| Day 180 | 17.55 ± 0.46 | 16.71 ± 0.50 |
| Day 240 | 17.21 ± 0.36 | 18.20 ± 0.14 |
| Day 360 | 25.70 ± 0.55 | 24.37 ± 0.36 |

*P1 is a mixture of Sodium Benzoate (0.25%) + Citric acid (0.05%); and RT is room temperature.

The effectiveness of the preservative of the present invention in maintaining the stability of hormones in liquid biological samples was evaluated by measuring the maintenance of base-line physiological levels of melatonin and cortisol in saliva. Aliquots (non-spiked) of the pooled saliva samples containing base-line physiological levels of melatonin and cortisol were stored −20° C. or at room temperature and containing sodium benzoate and citric acid in an amount of 0.25% and 0.05% of the sample (weight/volume), respectively ("P1"). Duplicate samples were analyzed by radioimmunoassay on days 1, 14, 28, 60, 120, 180, 240 and 360 (see Tables 5 and 6 below). Melatonin and cortisol concentrations were comparable in saliva samples stored for 180 days at −20° C. and at room temperature in the presence of P1.

TABLE 5

SALIVA STABILITY OF MELATONIN (pg/ml) UNDER VARIED PRESERVATION CONDITIONS

| Time | Melatonin (P1)* [RT] | No Preservative [−20° C.] |
| --- | --- | --- |
| Day 01 | 18.73 ± 0.02 | 18.98 ± 2.7 |
| Day 14 | 26.22 ± 3.03 | 17.94 ± 0.07 |
| Day 28 | 31.71 ± 4.4 | 29.43 ± 5.9 |
| Day 60 | 21.33 ± 4.5 | 14.37 ± 0.64 |
| Day 120 | 25.08 ± 5.6 | 19.59 ± 1.5 |
| Day 180 | 24.02 ± 3.9 | 20.48 ± 0.04 |
| Day 240 | 10.78 ± 0.53 | 7.08 ± 0.53 |
| Day 360 | 14.95 ± 0.12 | 6.96 ± 0.007 |

*P1 is a mixture of Sodium Benzoate (0.25%) + Citric acid (0.05%) and RT is room temperature.

TABLE 6

Saliva Stability Of Cortisol (μg/ml) Under Varied Preservation Conditions

| Time | Cortisol (P1*) [RT] | No Preservative [−20° C.] |
| --- | --- | --- |
| Day 01 | 1.46 | 1.37 |
| Day 14 | 1.34 | 1.29 |
| Day 28 | 1.38 | 1.29 |
| Day 60 | 1.28 | 1.25 |
| Day 120 | 1.07 | 1.19 |
| Day 180 | 0.97 | 1.09 |
| Day 240 | 0.10 | 0.70 |
| Day 360 | 0.05 | 0.75 |

*P1 is a mixture of Sodium Benzoate (0.25%) + Citric acid (0.05%) and RT is room temperature.

EXAMPLE 2

An Apparatus for Preserving a Liquid Biological Sample

Another aspect of the invention is an apparatus for preserving a liquid biological sample. The apparatus includes a vessel for collecting and storing a liquid biological sample and a preservative which is disposed within the vessel. The preservative includes sodium benzoate and citric acid in an amount of about 0.15% to about 1.00% and about 0.025% to about 0.200% of the sample (weight/volume), respectively. The preservative disposed within the vessel is preferably a dry solid, but may be in the form of a paste, a liquid, a gel, a tablet or a capsule. The apparatus is useful for preserving saliva and may be useful for preserving a variety of liquid biological samples including, but not limited to, saliva, tears, urine, blood, serum, plasma, sweat, vaginal fluids, semen, feces, mucous, breast milk, ascites, pleural effusion, synovial fluid, bone marrow, lymph, spino-cerebral fluid, and washings from bodily cavities (e.g., lung washings).

Referring to FIG. 1, preservative 10 is deposited on interior surface 12 of vessel 14. Any interior surface of vessel 14 will suffice, however, deposition on an interior surface near terminal end portion 16 facilitates combining the sample with preservative 10. Although preservative 10 may be deposited in vessel 14 by a variety of methods, vacuum drying a solution containing sodium benzoate and citric acid is preferred. Because the preservative is vacuum dried, the shelf life of this apparatus is significantly extended as compared to a preservative in liquid form. Moreover, vacuum drying facilitates easy storage and transportation of vessels, substrates, absorbent masses or other materials to which the preservative may be coupled (e.g., by eliminating spillage problems).

Referring to FIG. 2, alternatively, the apparatus includes storage vessel 18, collection device 20 and cap 22. Vessel 18 includes vessel wall 24 which extends between closed end 26 and lip 28. Preservative 19 is deposited on an interior surface of vessel 18 near closed end 26. Collection device 20 is disposed substantially within storage vessel 18 and includes wall 30. Wall 30 extends between apertured floor 32 and shoulder 34, which terminates in upright arm 36. The position of collection device 20 is fixed by the interaction of shoulder 34 with lip 28. Collection device 20 also includes absorbent mass 38 for collecting a liquid biological sample. Cap 22 includes top 40 from which cap wall 42 downwardly extends and terminates in flange 44. Cap 22 may be inserted into collection device 20 such that flange 44 is adjacent upright arm 36. Cap 22 may be removed and absorbent mass 38 used to collect a liquid biological sample (see e.g., Hebel et al., U.S. Pat. No. 4,774,962). Absorbent mass 38 may then be returned to collection device 20 and the sample extracted by centrifugation or other methods. Extraction results in separation of the sample from absorbent mass 38, passage of the sample through apertured floor 32 and combining of the sample with preservative 19 at closed end 26. Alternatively, following extraction, cap 22 may be removed, collection device 20 discarded and cap 22 inserted into vessel 18.

In another aspect of the invention, an apparatus which may be useful for preserving a liquid biological sample includes an absorbent mass for collecting the sample and a preservative coupled operatively to the mass. The preservative includes sodium benzoate and citric acid in an amount of about 0.15% to about 1.00% and about 0.025% to about 0.200% of the sample (weight/volume), respectively. The preservative may be coupled operatively to the mass by a variety of methods (e.g., impregnation or coating). For example, the absorbent mass may be impregnated with the preservative by absorbing a solution of sodium benzoate and citric acid in an amount of about 0.15% to about 1.00% and about 0.025% to about 0.200% of the absorptive capacity of the absorbent mass (weight/volume), respectively. Alternatively, the solvent in which the preservative is contained may be either completely or partially evaporated. The volume and concentration of the preservative solution required may be calculated by determining the absorptive capacity of the mass and the volume of the sample to be collected. The absorbent mass may then be used to collect a liquid biological sample and placed in a storage vessel to await analysis. Alternatively, the absorbent mass may be placed in a collection device (see FIG. 2 and discussion above) and centrifuged to separate the sample from the absorbent mass. Where the preservative has been coupled operatively to the absorbent mass it need not be deposited within the storage vessel.

In another aspect of the invention, an apparatus which may be useful for preserving a liquid biological sample includes a substrate to which a preservative has been operatively coupled. The preservative includes sodium benzoate and citric acid in an amount of about 0.15% to about 1.00% and about 0.025% to about 0.200% of the sample (weight/volume), respectively. The substrate may be a filter, a membrane or other material to which the preservative may be releasably bound. Preferred substrates include ten millimeter diameter disks of Whatman No. 1 filter paper or polyethylene terathalate. The preservative may be coupled operatively to the mass in a manner similar to that described above for the absorbent mass (e.g., impregnation or coating). The preservative is coupled to the substrate such that it is readily dissolved upon contact with the sample. The apparatus may also include a vessel into which the substrate may be placed. The substrate may be placed in the vessel either prior to or after the addition of a liquid biological sample.

Referring to FIG. 3, substrate 46 may be disposed within collection device 48 below the absorbent mass (not shown) adjacent apertured floor 50. Collection device 48 containing substrate 46 is utilized in conjunction with storage vessel 18 and cap 22 as described essentially for FIG. 2 with the exception that the preservative is deposited on or within substrate 46 (i.e., not deposited within vessel 18). In this embodiment, following collection of the sample, the absorbent mass is inserted into collection device 48 above substrate 46 such that centrifugation of the apparatus causes the liquid biological sample to be extracted from the absorbent mass, mixed with the preservative of substrate 46, and passed through the apertured floor to collect at the sealed end of the vessel. Alternatively, the substrate may be positioned within the storage vessel adjacent the sealed end.

EXAMPLE 3
An Apparatus for Preserving a Saliva Sample

An apparatus for preserving a saliva sample, essentially as shown in FIG. 2 and described above, may be produced by modifying a commercially available salivette (e.g., Sarstedt* Model No. 55.524PP). The vessel is separated from the collection device and a 0.2 ml aliquot of a 2.5% sodium benzoate and 0.5% citric acid solution is added to the vessel. A uniform deposition of preservative may be achieved at the closed end of the vessel by drying the solution with a speed-vac (Savant* Model No. SVC 100 H). This apparatus is suitable for collecting, preserving and storing saliva samples ranging in volume between about 0.5 ml and about 4.0 ml (i.e., resulting in final concentrations of sodium benzoate and citric acid of about 0.15% to about 1.00% and about 0.025% and about 0.200% of the sample (weight/volume), respectively). After drying, the apparatus is reassembled by inserting the collection device and the cap into the storage vessel.

EXAMPLE 4
A Method of Preserving a Liquid Biological Sample

Another aspect of this invention is a method of preserving a liquid biological sample for a period of time heretofore unknown in this art. The method includes the steps of providing a liquid biological sample and combining the sample with a preservative containing sodium benzoate and citric acid in an amount of about 0.15% to about 1.00% and about 0.025% to about 0.200% of the sample (weight/volume), respectively. The method is effective for preserving saliva and a variety of liquid biological samples including, but not limited to, tears, urine, blood, serum, plasma, sweat, vaginal fluids, lymph, semen, feces, mucous, breast milk, ascites, pleural effusion, synovial fluid, bone marrow, spino-erebral fluid, and washings from bodily cavities (e.g., lung washings). The preservative is preferably a dry solid, but may be supplied in a variety of forms (e.g., paste, liquid, gel, tablet or capsule). In an alternative embodiment, after the step of providing, the sample is introduced within a vessel into which the preservative in solid form has been disposed. The preservative is preferably adhered to an interior surface of the vessel by vacuum drying a solution containing sodium benzoate and citric acid thereon. However, other methods of disposing the preservative within the vessel may be used.

The method may also include the steps of collecting a sample in an absorbent mass and separating the sample from the absorbent mass. Following collection, the sample may be separated from the mass by compression, centrifugation, capillary action or other methods. Preferably, the sample is separated by inserting the mass into a vessel having upper and lower chambers separated by a liquid permeable partition. The vessel is centrifuged such that the sample passes through the partition into the lower chamber having the preservative disposed therein. The mass is retained in the upper chamber of the vessel and the sample collects in the lower chamber and combines with the preservative.

Alternatively, a modification of this method which may be useful for preserving a liquid biological sample includes collecting the sample with an absorbent mass to which the preservative has been operatively coupled. The sample, now combined with the preservative, may be retained in the absorbent mass until analyzed or it may be separated as described above. Because the preservative is coupled operatively to the absorbent mass, it need not be disposed within the lower chamber of the vessel.

In another alternative method which may be useful for preserving a liquid biological sample, the preservative is operatively coupled to a substrate. The substrate may be a filter, a membrane, or other suitable material to which the preservative may be releasably bound. The sample may be combined with the preservative by placing the substrate within a vessel either before or after addition of the sample. Moreover, where the vessel has an upper and a lower chamber separated by a liquid permeable partition, the substrate may be placed in either chamber to accomplish the combining step. The sample may be provided directly into a vessel containing the substrate or alternatively, may be collected in an absorbent mass and extracted by compression, centrifugation or other methods. Preferably, the absorbent mass is placed on top of the substrate in the upper chamber of a vessel. The vessel may then be centrifuged so that the sample passes through the substrate, combines with the preservative and collects in the lower chamber of the vessel. The absorbent mass and substrate are retained within the upper chamber.

An alternative method which may be useful for preserving a saliva sample includes the steps of introducing a preservative into the oral cavity of a mammal and collecting a saliva sample from the manual. The preservative is preferably edible and contains sodium benzoate and citric acid in an amount of about 0.15% to about 1.00% and about 0.025% to about 0.200% of the sample (weight/volume), respectively. Alternatively, the preservative may be coupled operatively to a vehicle (e.g., a paste, powder, liquid, gel, tablet or capsule) which may be introduced into the oral cavity of a mammal.

EXAMPLE 5
A Method for Preserving a Saliva Sample

The apparatus described in Example 2 may be used in a method of preserving saliva samples. The cap is removed from the collection device so that the absorbent mass may be extracted. The absorbent mass is placed into the oral cavity of a mammal from which a saliva sample is desired. Although the absorbent mass may be simply retained in the oral cavity until the desired volume of saliva is absorbed, mastication of the absorbent mass facilitates sample collection. Following collection, the absorbent mass is returned to the collection device and the cap is replaced in its original position. The apparatus is then centrifuged at 3000 revolutions per minute for ten minutes in order to separate the sample from the absorbent mass. The absorbent mass is retained in the collection device and the sample passes through the apertured floor and accumulates at the closed end of the vessel where it combines with the preservative. Following separation, the collection device may be discarded and the storage vessel sealed with the cap. Saliva samples preserved according to this method have been stored for extended periods without refrigeration or freezing. Therefore, this method allows samples to be easily obtained and preserved for analysis in a variety of remote locations (e.g., during space travel, field research and non-clinical health care settings).

EXAMPLE 6
A method for preserving a plasma sample

The present technology discloses the requirements for biologic sample preservation at ambient temperature, i.e., development of a cost effective, generic technology that has application across several disciplines or programs and has a commercial potential. The efficacy of a preservative mixture in preserving biological samples at room temperatures when linked to an inert carrier (polyethylene terethalate) or coated to polypropylene tubes is described.

To prepare the preservative discs, custom made polyethylene terethalate discs (diameter 12 mm) were purchased from Venoject® supplies (Terumo Medical Services). Each disc was placed in a test tube containing the preservative solution for coating the disc. The tubes with the preservative solution and the discs were then be kept overnight in a hot air oven set at 40° C. The preservative gets adsorbed onto the discs as it evaporates. Once ready, the discs are taken out of the tubes and stored for use. Preservative coated tubes were prepared by adding 200 $\mu$l of preservative and air-dying them at 40° C. for 24 hours. The coated vials were stored at room temperature until use. A total of 20 mL blood was collected from each subject. Samples were collected by venipuncture into two heparinized vacutainer™ tubes (10 mL). Samples were centrifuged and serum separated for later distribution as described below.

Serum aliquots (2.5 mL) were pipetted into polypropylene tubes for preparation and analysis at a later date. The samples were divided into three sets of 10 samples each, two sets for ambient storage at room temperature and the other for storage in a freezer at −20° C. Preservative discs were added (one per tube) to one set of tubes that will be stored at room temperature. Preservative coated tubes were used as the second set of tubes for samples stored at room temperature. Samples were analyzed on 0, 1, 3, 7, 14, 21, 28, 45, 75, and 90 days of storage. The day 0 data served as reference control. Serun aliquots (2.5 mL) were used for biochemical analytes stability studies The biochemical variables measured were the routine serum chemistries (glucose, cholesterol, triglycerides, electrolytes [Na, K, Cl], creatinine, blood urea nitrogen [BUN], lactate dehydrogenase [LDH], alanine transaminase [ALT], aspartate transaminase [AST], creatine kinase [CK], and alkaline phosphatase. Each sample was analyzed by duplicate injections. The freezer (−20° C.) samples served as gold standards, and were analyzed along with the samples at room temperature on the days mentioned. Samples without the preservative were not included in the set at room temperature, since these samples would be contaminated with fungal growth and would be destroyed in less than 7 days. In addition to these biochemical analyses, microbial growth (fungi and bacteria) and counts (if any) were performed with all samples on the same days as those for stability analyses, to assess sample integrity and bacteriostatic effect of the preservative.

Samples were analyzed for determining biochemical analyte levels according to the standard methods of analyses in the Beckman Synchron CX®/CX®5 systems. Microbial analyses of biological samples was done after serum was plated out on blood agar using the spread plate technique. Microbial quantification (in CFU/mL) and complete identification to genus level was performed for each sample.

As demonstrated herein, a mixture of sodium benzoate and citric acid added to saliva samples after collection and stored at ambient temperatures for several days, effectively preserved endogenous compounds, melatonin and cortisol (180 days) and pharmaceuticals acetaminophen (APAP) and antipyrine (AP) (360 days). In addition, this preservative mixture was coated onto the bottom of saliva collection tubes (Salivettesg) and used for sample collection and storage during a Mir-space flight mission. Results indicated that APAP and AP concentrations were stable in saliva stored in the locker of the Shuttle over 90 days.

To refine the existing technology and make it more applicable to the preservation of other biological samples, e.g., blood, the preservative mixture was coated on to an inert carrier surface such as the polyethylene terethalate discs. Dispensing the preservative in a solid form has other advantages as well. First, it will not affect analyte concentrations due to volume changes resulting from the addition of a liquid preservative; second, it does not require any volume measurements and liquid dispensing systems that will be difficult to use in space; third, the discs can be used with any aqueous sample type, and fourth, it can be used with any collection device with no special preparation of the device. Polyethylene terethalate discs are routinely used in clinical chemistry and microbiology labs as inert carriers of active substances and are commercially available.

The preservation of serum samples was evaluated in polyethylene terethalate discs for 90 days. Tables 7–9 shows the comparison of data from the preservative coated devices (discs and tubes) along with the −20° C. frozen samples indicates that both preservative coated polyethylene terethalate discs and preservative coated tubes are effective in preserving serum electrolytes, glucose, BUN, creatinine, cholesterol, alkaline phosphatase and LDH over the study period. The preservative mixture was effective in maintaining the stability for seven days with respect to ALT, AST and CK. However, with respect to triglycerides there was an interference which increased over the study period. No microbial growth was noticed in samples preserved with polyethylene terethalate discs or in preservative coated tubes stored at room temperature during the study period.

TABLE 7

Chemistry Profile in Serum Samples with Polyethlene Terethallate Discs

| Days | Glucose mg/dl | BUN mg/dl | Creatinine mg/dl | Cholesterol mg/dl | Triglycerides mg/dl | AST U/L | ALT U/L | ALK Phos U/L | CK U/L | LDH U/L | Sodium mmol/L | Potassium mmol/L | Chloride mmol/L |
|---|---|---|---|---|---|---|---|---|---|---|---|---|---|
| Day 0  | 98  | 15 | 0.9 | 181 | 88  | 20 | 18 | 54 | 70 | 119 | 158 | 4.3 | 110 |
| Day 0  | 99  | 15 | 1   | 182 | 88  | 21 | 20 | 56 | 68 | 120 | 155 | 4.3 | 108 |
| Day 3  | 97  | 16 | 1   | 188 | 94  | 20 | 18 | 61 | 66 | 121 | 157 | 4.3 | 110 |
| Day 3  | 97  | 16 | 1   | 186 | 94  | 19 | 18 | 61 | 68 | 121 | 156 | 4.2 | 111 |
| Day 7  | 99  | 16 | 1   | 186 | 104 | 17 | 18 | 60 | 63 | 119 | 157 | 4.2 | 107 |
| Day 7  | 88  | 16 | 1   | 184 | 104 | 18 | 18 | 62 | 64 | 116 | 155 | 4.3 | 107 |
| Day 14 | 96  | 16 | 1   | 179 | 110 | 19 | 15 | 58 | 58 | 117 | 157 | 4.3 | 108 |
| Day 14 | 97  | 16 | 1   | 179 | 110 | 16 | 13 | 58 | 59 | 119 | 155 | 4.2 | 110 |
| Day 21 | ND  | 18 | 1.3 | 183 | 98  | 37 | ND | 58 | 46 | 115 | 161 | 4.6 | 110 |
| Day 21 | 99  | 16 | 0.9 | 182 | 118 | 15 | 13 | 60 | 56 | 116 | 158 | 4.2 | 112 |
| Day 28 | 100 | 16 | 1   | 183 | 126 | 12 | 11 | 59 | 55 | 118 | 158 | 4.3 | 108 |
| Day 28 | 100 | 16 | 1.1 | 182 | 138 | 12 | 11 | 58 | 54 | 117 | 156 | 4.3 | 106 |
| Day 45 | 95  | 17 | 1   | 173 | 148 | 8  | 6  | 62 | 46 | 111 | 156 | 4.3 | 106 |
| Day 45 | 95  | 16 | 1   | 175 | 147 | 7  | 6  | 62 | 47 | 110 | 156 | 4.3 | 108 |
| Day 75 | 96  | 17 | 1.1 | 175 | 170 | 2  | 3  | 61 | 41 | 105 | 158 | 4.3 | 106 |
| Day 75 | 95  | 17 | 1   | 172 | 170 | 2  | 1  | 63 | 42 | 108 | 158 | 4.3 | 108 |
| Day 90 | 95  | 18 | 1   | 175 | 179 | 1  | 1  | 61 | 33 | 100 | 155 | 4.3 | 106 |
| Day 90 | 94  | 18 | 1   | 174 | 174 | 0  | 2  | 60 | 35 | 102 | 157 | 4.3 | 105 |

TABLE 8

Chemistry Profile in Serum Samples in Preservative Coated Tubes
Chemistry Profile in Serum Samples Stored in −20° C. (Freezer)

| Days | Glucose mg/dl | BUN mg/dl | Creatinine mg/dl | Cholesterol mg/dl | Triglycerides mg/dl | AST U/L | ALT U/L | ALK Phos U/L | CK U/L | LDH U/L | Sodium mmol/L | Potassium mmol/L | Chloride mmol/L |
|---|---|---|---|---|---|---|---|---|---|---|---|---|---|
| Day 0  | 98  | 15 | 1   | 181 | 88  | 19 | 20 | 55 | 66 | 118 | 156 | 4.3 | 109 |
| Day 0  | 99  | 15 | 1   | 181 | 86  | 20 | 19 | 56 | 67 | 117 | 158 | 4.3 | 111 |
| Day 3  | 97  | 16 | 1   | 187 | 93  | 19 | 19 | 61 | 67 | 115 | 158 | 4.3 | 111 |
| Day 3  | 95  | 15 | 1   | 187 | 95  | 21 | 18 | 63 | 65 | 116 | 160 | 4.3 | 110 |
| Day 7  | 99  | 15 | 1   | 186 | 99  | 19 | 18 | 60 | 65 | 116 | 156 | 4.2 | 108 |
| Day 7  | 98  | 16 | 0.9 | 186 | 100 | 16 | 19 | 64 | 62 | 113 | 156 | 4.3 | 108 |
| Day 14 | 96  | 16 | 1.1 | 181 | 111 | 16 | 14 | 58 | 58 | 118 | 155 | 4.2 | 108 |
| Day 14 | 98  | 16 | 1.1 | 180 | 108 | 15 | 15 | 57 | 58 | 116 | 156 | 4.3 | 108 |
| Day 21 | 98  | 16 | 1   | 182 | 114 | 15 | 15 | 62 | 56 | 118 | 155 | 4.3 | 109 |
| Day 21 | 99  | 16 | 1   | 183 | 112 | 13 | 14 | 59 | 57 | 116 | 156 | 4.3 | 110 |
| Day 28 | 99  | 17 | 0.9 | 183 | 122 | 13 | 13 | 60 | 54 | 117 | 156 | 4.3 | 106 |
| Day 28 | 101 | 16 | 1   | 183 | 191 | 12 | 11 | 57 | 55 | 118 | 158 | 4.3 | 106 |
| Day 45 | 94  | 17 | 1   | 174 | 147 | 9  | 5  | 62 | 48 | 105 | 155 | 4.3 | 108 |
| Day 45 | 95  | 17 | 1   | 173 | 143 | 8  | 6  | 60 | 47 | 109 | 157 | 4.3 | 108 |
| Day 75 | 96  | 17 | 1   | 173 | 169 | 4  | 2  | 61 | 42 | 106 | 159 | 4.3 | 106 |
| Day 75 | 95  | 17 | 1   | 175 | 165 | 2  | 3  | 62 | 41 | 106 | 159 | 4.4 | 108 |
| Day 90 | 95  | 18 | 1   | 177 | 172 | 0  | 2  | 62 | 33 | 102 | 155 | 4.3 | 106 |
| Day 90 | 98  | 18 | 1   | 173 | 171 | 3  | 0  | 59 | 36 | 101 | 159 | 4.3 | 107 |

TABLE 9

| Days | Glucose mg/dl | BUN mg/dl | Creatinine mg/dl | Cholesterol mg/dl | Triglycerides mg/dl | AST U/L | ALT U/L | ALK Phos U/L | CK U/L | LDH U/L | Sodium mmol/L | Potassium mmol/L | Chloride mmol/L |
|---|---|---|---|---|---|---|---|---|---|---|---|---|---|
| Day 0  | 100 | 15 | 0.9 | 182 | 88  | 20 | 17 | 56 | 70 | 122 | 139 | 4.3 | 109 |
| Day 0  | 99  | 15 | 0.9 | 182 | 87  | 22 | 19 | 56 | 70 | 122 | 142 | 4.3 | 110 |
| Day 3  | 96  | 15 | 0.9 | 187 | 90  | 20 | 18 | 64 | 69 | 118 | 140 | 4.2 | 110 |
| Day 3  | 97  | 15 | 1   | 186 | 90  | 20 | 18 | 63 | 68 | 119 | 140 | 4.2 | 109 |
| Day 7  | 99  | 16 | 1   | 187 | 89  | 21 | 19 | 61 | 69 | 120 | 140 | 4.2 | 107 |
| Day 7  | 100 | 16 | 0.9 | 188 | 90  | 20 | 17 | 63 | 70 | 117 | 138 | 4.2 | 107 |
| Day 14 | 98  | 15 | 1   | 184 | 96  | 20 | 16 | 59 | 65 | 119 | 139 | 4.2 | 108 |
| Day 14 | 98  | 16 | 1   | 186 | 95  | 18 | 16 | 59 | 66 | 118 | 139 | 4.2 | 111 |
| Day 21 | 99  | 15 | 1   | 187 | 99  | 20 | 15 | 62 | 67 | 118 | 140 | 4.3 | 110 |
| Day 21 | 99  | 15 | 1   | 188 | 94  | 21 | 15 | 64 | 67 | 119 | 142 | 4.3 | 111 |
| Day 28 | 100 | 16 | 1.1 | 185 | 89  | 18 | 15 | 61 | 64 | 117 | 139 | 4.2 | 107 |
| Day 28 | 100 | 16 | 1   | 187 | 90  | 17 | 14 | 60 | 64 | 116 | 140 | 4.3 | 107 |
| Day 45 | 95  | 15 | 1   | 184 | 96  | 19 | 14 | 61 | 59 | 107 | 139 | 4.2 | 108 |
| Day 45 | 95  | 15 | 1   | 185 | 104 | 20 | 13 | 62 | 61 | 111 | 139 | 4.2 | 107 |
| Day 75 | 96  | 16 | 1   | 181 | 98  | 20 | 13 | 59 | 60 | 107 | 140 | 4.3 | 105 |
| Day 75 | 96  | 16 | 1.1 | 181 | 101 | 21 | 13 | 59 | 61 | 107 | 140 | 4.2 | 106 |
| Day 90 | 96  | 16 | 1   | 183 | 97  | 20 | 11 | 54 | 54 | 106 | 139 | 4.2 | 105 |
| Day 90 | 96  | 16 | 1   | 187 | 99  | 18 | 9  | 59 | 50 | 107 | 139 | 4.2 | 106 |

Thus, the present invention also demonstrates that serum samples could be preserved for 90 days either in PET devices or PCTs at room temperature free from microbial growth. Moreover, serum chemistries such as electrolytes, glucose, creatinine, BUN, cholesterol, alkaline phosphatase, and LDH were stable at room temperature during the study period. Other serum enzymes (ALT, AST and CK) were stable only for seven days.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A kit for preserving a liquid biological sample comprising:
a preservative comprising sodium benzoate in an amount of about 0.15% to about 1.00% and citric acid in an amount of about 0.025% to about 0.200% of the sample (weight/volume); and a sample collecting device to which the preservative is operably linked, wherein said sample collecting device is an absorbent mass.

2. The kit of claim 1, wherein the liquid biological sample is selected from the group consisting of saliva, tears, urine, blood, serum, plasma, sweat, vaginal fluids, semen, feces, mucous, breast milk, ascites, pleural effusion, lymph, synovial fluid, bone marrow, spino-cerebral fluid, and washings from bodily cavities.

3. The kit of claim 1, wherein the preservative is selected from the group comprising a liquid, a paste, or a solid.

4. The kit of claim 1, wherein the preservative is operably linked by vacuum drying a solution comprising sodium benzoate and citric acid onto the absorbent mass.

5. The kit of claim 1, wherein the absorbent mass is placed in a storage vessel.

6. A kit for preserving a liquid biological sample comprising:
  a) a preservative comprising sodium benzoate in an amount of about 0.15% to about 1.00% and citric acid in an amount of about 0.025% to about 0.200% of the sample (weight/volume); a sample collecting device to which the preservative is operably linked, wherein said sample collecting device is an absorbent mass; and
  c) a storage vessel.

7. The kit of claim 6, wherein the preservative is selected from the group comprising a liquid, a paste, or a solid.

8. The kit of claim 6, wherein the preservative is releasably bound.

9. The kit of claim 6, wherein the preservative is operably linked by vacuum drying a solution comprising sodium benzoate and citric acid onto the absorbent mass.

10. The kit of claim 6, wherein the storage vessel is centrifugeable.

11. The kit of claim 6, wherein the storage vessel has an upper chamber separated by a liquid permeable partition from a lower chamber.

12. A kit for preserving a liquid biological sample comprising:
  a) a preservative comprising sodium benzoate in an amount of about 0.15% to about 1.00% and citric acid in an amount of about 0.025% to about 0.200% of the sample (weight/volume);
  b) a sample collecting device to which the preservative is operably linked, wherein said sample collecting device is an absorbent mass; and
  c) a disposable chamber with a liquid permeable floor.

13. The kit of claim 12, wherein the preservative is selected from the group comprising a liquid, a paste, or a solid.

14. The kit of claim 12, wherein the preservative is releasably bound.

15. The kit of claim 12, wherein the preservative is operably linked by vacuum drying a solution comprising sodium benzoate and citric acid onto the absorbent mass.

16. The kit of claim 12, wherein the disposable insert is centrifugeable.

17. A kit for preserving a liquid biological sample comprising:
  a) a preservative comprising sodium benzoate in an amount of about 0.15% to about 1.00% and citric acid in an amount of about 0.025% to about 0.200% of the sample (weight/volume);
  b) a sample collecting device to which the preservative is operably linked, wherein said sample collecting device is an absorbent mass;
  c) a disposable upper chamber with a liquid permeable floor and a lip; and
  d) a storage vessel with a shoulder wherein said disposable upper chamber is fixed by the interaction of the shoulder with the lip.

18. The kit of claim 17, wherein the preservative is selected from the group comprising a liquid, a paste, or a solid.

19. The kit of claim 17, wherein the preservative is releasably bound.

20. The kit of claim 17, wherein the preservative is operably linked by vacuum drying a solution comprising sodium benzoate and citric acid onto the absorbent mass.

21. The kit of claim 17, wherein the kit is centrifugeable.

* * * * *